(12) United States Patent
Choi

(10) Patent No.: US 9,662,247 B2
(45) Date of Patent: May 30, 2017

(54) PATCH FOR TREATING AND ALLEVIATING SYMPTOMS OF SKIN DISEASES ACCOMPANIED BY EFFUSION OF BLOOD PROTEINS

(71) Applicant: BIOPID CORPORATION, Chuncheon (KR)

(72) Inventor: Seong Hyun Choi, Chuncheon (KR)

(73) Assignee: BIOPID CORPORATION, Chuncheon-si (KR)

( * ) Notice: Subject to any disclaimer, the term of this patent is extended or adjusted under 35 U.S.C. 154(b) by 0 days.

(21) Appl. No.: 15/251,036

(22) Filed: Aug. 30, 2016

(65) Prior Publication Data

US 2016/0367407 A1    Dec. 22, 2016

Related U.S. Application Data

(63) Continuation of application No. 13/809,429, filed as application No. PCT/KR2011/005061 on Jul. 11, 2011, now abandoned.

(30) Foreign Application Priority Data

Jul. 12, 2010  (KR) .................. 10-2010-0066981

(51) Int. Cl.
| | | |
|---|---|---|
| A61F 13/00 | (2006.01) | |
| A61M 35/00 | (2006.01) | |
| A61K 9/70 | (2006.01) | |
| A61L 15/16 | (2006.01) | |
| A61L 15/00 | (2006.01) | |
| A61K 31/545 | (2006.01) | |
| A61B 5/00 | (2006.01) | |
| A61K 31/717 | (2006.01) | |
| A61K 31/74 | (2006.01) | |
| A61L 15/20 | (2006.01) | |
| A61L 15/22 | (2006.01) | |
| A61L 15/42 | (2006.01) | |

(52) U.S. Cl.
CPC ........ *A61F 13/00042* (2013.01); *A61B 5/443* (2013.01); *A61F 13/00017* (2013.01); *A61F 13/00063* (2013.01); *A61K 9/703* (2013.01); *A61K 31/545* (2013.01); *A61K 31/717* (2013.01); *A61K 31/74* (2013.01); *A61L 15/20* (2013.01); *A61L 15/225* (2013.01); *A61L 15/42* (2013.01); *A61M 35/00* (2013.01)

(58) Field of Classification Search
None
See application file for complete search history.

(56) References Cited

U.S. PATENT DOCUMENTS

| | | | |
|---|---|---|---|
| 4,537,767 A | 8/1985 | Rothman | |
| 5,155,144 A | 10/1992 | Manganaro | |
| 5,558,861 A | 9/1996 | Yamanaka | |
| 2009/0318843 A1* | 12/2009 | Van Holten | A61L 31/10 602/52 |

FOREIGN PATENT DOCUMENTS

| | | |
|---|---|---|
| CN | 101036591 | 9/2007 |
| EP | 0210756 | 2/1987 |
| EP | 0395476 | 10/1990 |
| GB | 873903 | 8/1961 |
| WO | 2007/127390 | 11/2007 |
| WO | 2009-064963 | 5/2009 |

OTHER PUBLICATIONS

Australian Patent Office, Examination Report of Australian Patent Office dated Aug. 23, 2013, in Application No. 2011277310.
Office Action, State Intellectual Property Office of the P.R.C(SIPO), Feb. 27, 2014, Chinese Patent Application No. 201180034702.6.
The Search Report, Jul. 28, 2015, European Patent Office, Application No. 11807003.6.

* cited by examiner

*Primary Examiner* — Jeffrey T Palenik
(74) *Attorney, Agent, or Firm* — Lex IP Meister, PLLC

(57) ABSTRACT

Provided is a patch for treating skin diseases or alleviating symptoms of the skin diseases involving an exudation of blood proteins, or for absorbing blood proteins exuded to the skin.

7 Claims, 11 Drawing Sheets

Example of Applying to Child with Severe Atopic Dermatitis (Leg Region)

Analysis of Proteins obtained from Patch after Applying to Diseased Area

Example of Applying to Child of Severe Atopic Dermatitis (Calf Region)

[Applying the patch containing a composition of phospholipids extracted from a pig lung ]

Analysis of Proteins obtained from Patch After Applying to Diseased Area

Example of Applying to Face with Atopic Dermatitis

Analysis of Proteins obtained from Patch After Applying to Face

Example of Applying Double Patch with Different Polarities

Analysis of Proteins obtained from Double Patch with Different Polarities after Applying to Diseased Area Psoriasis Exudation Proteins Pattern   Atopic Exudation Proteins Pattern Example of Applying to Wound (Negative Effect)

Before applying    After 8 hours

Blood coagulation proteins
absorbed to patch    After 22 days

Mimetic Diagram of Process of Preparing DEAE-cotton Fabrics

PATCH FOR TREATING AND ALLEVIATING SYMPTOMS OF SKIN DISEASES ACCOMPANIED BY EFFUSION OF BLOOD PROTEINS

CROSS-REFERENCES TO RELATED APPLICATION

This application is a Continuation Application of U.S. patent application Ser. No. 13/809,429 filed on Jan. 10, 2013, which is a National Stage application of PCT/KR2011/005061 filed on Jul. 11, 2011, which claims priority to Korean Patent Application No. 10-2010-0066981 filed on Jul. 12, 2010, the contents of which are incorporated herein by reference.

TECHNICAL FIELD

The present invention relates to a patch for treating skin diseases and alleviating symptoms of the skin diseases involving an exudation of blood proteins, or for adsorbing blood proteins that is exuded to skin.

BACKGROUND ART

New Theory on Causes of Atopic Diseases

Various factors such as genetic factors, the pollen, dust mites, chemicals, for example, formaldehydes, and westernized food are regarded as a cause that leads to an atopic disease. However, the accurate cause of the disease is not clear still. As immunological consequences exhibited in atopic diseases, there are unique characteristic that Th1 cells are activated when epidermis is infected, and also Th2 cells are actively active as one of phenomena, which are exhibited at the time of continuously exposing to huge antigens, such as parasitization, or a kind of mechanism for controlling immunomodulary. The present invention has no the emphasis on the unique immunological phenomena exhibited in the atopic diseases. However, in the present invention, it is considered that the phenomenon of permeating blood proteins exuded from blood vessel into skin tissues due to metabolism imbalance or metabolic disorder of body is the start and fundamental cause of an atopic disease. Thus, it is believed that immune reactions generated in atopic diseases are caused by an exudation of blood proteins. Based on the above consideration, the present invention tried to solve the problems. Furthermore, it is also considered that psoriasis is caused by an exudation of blood proteins, and thus the present invention suggests a new therapy for treating psoriasis based on the above cause.

Prior to the 1980's (prior to the 1970's in USA or UK), the frequency of a patient suffered from an atopic disease is not very high, and it has never been a social problem. However, since the late 1980's, the frequency of a patient suffered from an atopic disease has drastically increased, and recently, one of five elementary school students shows symptoms of an atopic disease. Accordingly, an atopic disease became a serious social problem. Comparison between the 1970's and 2000's indicates that air pollution decreases significantly as compared with that of 20 to 30 years ago due to prohibition of use of leaded gasoline, strong government regulation on an automobile exhaust discharge, an introduction of a public transportation using natural gas, a regulation of plant dust, a policy of grouping (making an industrial complex) plants discharging pollutants, and the like. For this reason, it is believed that the patients suffered from an atopic disease are not increased by the current environment and conditions.

The current living space has a much larger window than that in the housing of the 1970's, and the structure is changed such that the indoor of the housing receives much more light of the sun. A vacuum cleaner with a micro-filter is becoming more and more common, a washing machine with a bactericidal function is used, and detergents are getting stronger and are diversified. Dust mites are difficult to live in the current conditions than in previous years. That is, it is difficult to explain the relationship between the frequency of atopic diseases occurrence and dust mites. There are various grasses in a rural area as compared with the city. The concentration of pollen is far higher in a rural area as compared with the city. However, the frequency of atopic disease occurrence in the city is higher than that in a rural area. There is no relationship between the concentration of pollen and the frequency of atopic disease occurrence. Thus, it is difficult to consider pollen as a cause of atopic disease.

The things that are conspicuously changed in the city culture as compared with the 1970's includes a caterer's shop, various fast-food restaurants, a convenient public transportation system, a private car, and the like. Furthermore, since the mid-1980's, the most notable change is a change of food, and specifically, cooking oils (soybean oils, corn oils, olive oils, grape seed oils, cottonseed oils, and the like) and the like are supplied in bulk at a low cost. Thus, food heated in oil using these oils become popular unexpectedly. Additionally, margarine containing a large quantity of trans-oil and linoleic acid becomes popular. In accordance with the advertisement that margarine lowers a level of cholesterol and thus is good for one's health, margarine consumption had sharply increased for a while. Actually, most commercialized vegetable oil products are produced by an extraction process using solvent (for example, n-hexane). As a result, the most commercialized vegetable oil products are pure neutral lipids in a very clear and transparent state with no polar lipids, containing a great quantity of unsaturated fatty acid. In terms of an evolutionary process of human, it can be easily inferred that people take currently in too much vegetable neutral lipids having a great quantity of unsaturated fatty acid. That is, it is believed that there is a physiologically revolutionary change that can greatly affect a lipid metabolism of human. From a long evolution, human has eaten fatty acid containing cis-type fatty acid in natural state, but now a great quantity of trans-type fatty acid. As a result of evolution, human body does not have enzyme capable of converting trans-type fatty acid into cis-type fatty acid. An ingestion of trans-type fatty acid allows the whole lipid metabolism to slow down. Due to developments of public transportation and convenience, the physical activity level is rapidly decreased, and thereby the condition incapable of converting the ingested fatty acid into energy in a human body is formed. In addition, it may be considered that a living temperature accepted by a human body is sharply increased due to developments of heating system and clothing materials.

In conclude, it may be considered that the conditions have been made to be good for generating skin diseases such as an atopic disease and psoriasis since the imbalance of lipid metabolism is caused due to a decrease of the conversion of lipids into energy, overindulgence of neutral lipids containing unsaturated fatty acid, an intake of trans-oil, and a decrease of physical activity level, and the environment that can make an extension of capillary and uncompleted function of capillary is made due to an increase of living temperature.

Differences and Similarities Between Psoriasis and Atopic Disease

A defunctionalization of lung because of ingesting a great quantity of vegetable unsaturated fatty acid can be definitely known from a result of researching by Wolfe et al. (Wolfe R. R., Martini W. Z., Irtun O., Hawkins H. K., Barrow R. E. (2002) Dietary fat composition alters pulmonary function in pigs. Nutrition. 18:647-653). A compliance of lung tissue is lost, and blood plasma proteins are exuded by ingesting vegetable oils thereby affecting the functions. Similarly, skin may be affected by ingesting a great quantity of unsaturated fatty acid. The patients suffered from an atopic disease have high level of HDL-cholesterol (Schafer T., et al., (2003) Intake of unsaturated fatty acids and HDL cholesterol levels are associated with manifestations of atopy in adults. Clin. Exp. Allergy. 33:1360-1367). It can be interpreted that after ingesting lipid, active lipids are delivered to each organs. A delivery of lipids containing unsaturated fatty acid to skin may affect membrane components of epidermal cells and vascular cells, and the unsaturated fatty acids having high fluidity may reduce functions of blood vessel, thereby causing an exudation of blood plasma proteins, particularly albumin and immunoglobulin G (IgG). Such an exudation is accomplished through a gap between blood vessel cells, and as its evidence, sizes of proteins thus exuded are limited. IgG having a size of 150 KDa is easily exuded, but the proteins having larger size than that of the IgG described above are not easily exuded. Such an exudation mechanism can be exhibited in a patient suffered from psoriasis as well as a patient suffered from an atopic disease. It may be deduced that erythroderma or edema exhibited in psoriasis and an atopic disease may occur by generating a change of function or structure of blood vessel except for the case by infection or strong physical stimulation. It is important that psoriasis and atopic diseases are greatly different metabolically. Although the patients suffered from an atopic disease have high level of HDL-cholesterol, the patients suffered from psoriasis have very high levels of blood cholesterol and triacylglycerol. Interestingly, a size of sebaceous gland secreting the production of sebum of neutral lipid components in the patients suffered from psoriasis is too small. According to a simple analysis, it is shown that there may be a problem with the supply of lipids required for synthesizing sebum from blood vessel. A similar case for an atopic disease is that ceramide lipid required for protecting skin is low in epidermis. Although the profiles of lipids contained in the blood of psoriasis and atopic disease are different, an active lipid metabolism in the body is common ground between them. The common ground that is especially worth of notice in the psoriasis and atopic disease is an exudation of blood protein generated in both of the diseases. It can be deduced that although lipid metabolism is actively generated in the body, there may be a problem with a process of delivering lipids to epidermis, or special lipids that are necessarily required are not delivered to epidermis.

New Understanding on Inflammatory Response and Exudation of Blood Protein

The common ground between psoriasis and an atopic disease is that blood proteins are leaked from micro vascular and then exuded to a skin tissue. The exuded proteins have a limited molecular weight, and a large percentage of immunoglobulin G (IgG, 150 KDa) and serum albumin (66 KDa) is contained. It may be expected that the proteins exuded to skin may be slowly dried, bound randomly (random binding with low-affinity), non-specifically bound not selectively bound, or aggregated with each other while increasing an around salt concentration, not like the proteins inside the blood vessel. It may be deduced to continuously generate a vicious circle such that an exuded amount greatly increases by promoting a secretion of histamine due to a physical stimulation through scratching and generating uredo while drying the proteins. It may be deduced that since although there are no allergens or infection invaded from the outside, the phenomenon of non-specific or random aggregation of exuded antibodies can be recognized as a similar signal in the case of the infection, first neutrophils are moved to a tissue, and thus various immune cells may be recruited. Especially, it is illustrated that the phenomenon of recruiting macrophages in a tissue in the cases of chronic atopic diseases is generated by an immunological mechanism of Th2 cells due to a continuous antigen exposure. However, it can be illustrated that such the phenomenon is simply generated by a mechanism for cleaning the aggregation of exuded blood proteins. An example of such a cleaning mechanism includes a clear-up of agglomerated clots of surfactant proteins and lipids by macrophages in an idiopathic alveolar proteinosis. It is possible to explain the movement and activation of eosinophil observed in an atopic disease with regard to a protein exudation symptom. It is well known that eosinophil secretes cationic proteins. It may be one of a simple cytological mechanism for removing the exuded proteins after agglomerating the exuded proteins. Furthermore, it may be simply understood that eosinophil may be recruited in a region of exudation in order to reduce a blood protein exudation that is continuously generated in an atopic disease, like a recruitment of eosinophil in order to control or reduce a blood protein exudation after recruiting eosinophil by infection or sensitization of allergen in pleural cavity.

New Method for Solving Psoriasis and Atopic Disease

Based on the basis suggested above, if the psoriasis and atopic diseases are commonly generated by an imbalance and abnormal of lipid metabolism, and as a result, various inflammatory responses are induced by leaking and then agglomerating the blood proteins leaked from blood vessel in a tissue, a new method for treating the above diseases may be suggested.

As a method for treating the diseases that are most important and preceded, an ingestion of vegetable oils, especially vegetable neutral oils should be suppressed, and food that are cooked by not using a method of producing trans-oils in a cooking process or food containing trans-oils should be ingested. Since such a diet control method should be carried out until lipid components in the body are changed in a certain level, the method requires a considerable amount of time and energy. There are problems that since the patients with an atopic disease suffer from a severe itching, a period for treating the disease is long, but a diet control method must be used.

A second method is a method for alleviating inflammation and then recovering epidermis in a normal state by suppressing a blood protein exudation locally in a diseased area. Such a method is the method previously suggested by the present inventors that is registered as a patient in Australia, Singapore, and Russia in addition to Korea now (Korean Patent No. 0891595, Australia Patent No. 2006217261, PCT Patent No. PCT/KR2006/000638). The method is that the lipid metabolism in relevant cells and vascular cells is changed and an exudation of blood proteins is suppressed by applying the composition including disaturated phospholipids that are present in a great quantity in lung of animal to the diseased area. Such the method requires a treatment period, i.e., 8 to 12 weeks averagely, and in the case of the patient with severe symptoms, it is required for longer periods of time.

A third method is a method suggested in the present patient, and for removing exuded proteins permeated into a diseased area by using a patch for absorbing proteins. It is a method that a most rapid treatment period may be expected, i.e., averagely 10 days, and it is a very stable method since it is not a way for delivering any materials or effective components to skin and quickly alleviates the pain generated by a itching. However, there is the potential for the symptom to reoccur since the proteins may be re-exuded if the method is used without decreasing or suppressing the exudation of blood proteins. A non-recurrent and complete treatment can be expected for a short period of time by simultaneously applying a patch for removing an exudate of blood proteins suggested in the present patient in conjunction with a treatment for suppressing a protein exudation using various ways.

DISCLOSURE

Technical Problem

The present invention is devised for solving the above problems and the above needs, and an object of the present invention is to provide a patch for treating and alleviating symptoms of skin diseases involving an exudation of blood proteins.

Technical Solution

In order to achieve the above object, an exemplary embodiment of the present invention provides a patch for treating skin diseases or alleviating symptoms of the skin diseases involving an exudation of blood proteins, the patch including a) a polymer matrix with a micro-mesh structure; and b) a polar resin bonding with the proteins included in the matrix and/or a resin hydrophobic-bonded with the proteins included in the matrix.

According to an embodiment of the present invention, the polymer matrix with the micro-mesh structure may be preferably a micro-mesh structure of complex carbohydrate selected from the group consisting of agar and agarose, and a micro-mesh structure using polyacrylamide, latex, polystyrene, polyvinyl chloride, silicone, polyurethane, or cellulose fiber, but the present invention is not limited thereto.

According to an embodiment of the present invention, the polar resin includes an organic or inorganic matrix including a functional group that is ionic or capable of ionizing under a proper pH condition. The organic matrix may be a synthetic material (for example, acrylic acid, methacrylic acid, sulfonate styrene, sulfonate divinylbenzene) or a partial-synthetic material (for example, modified cellulose and dextran). Preferably, the inorganic matrix includes silica gel modified by adding an ionic group. The covalent-bonded ionic group may be strong acid (for example, sulfonic acid and phosphoric acid), weak acid (for example, carboxylic acid), strong base (for example, primary amine), weak base (for example, quaternary amine), or combination of an acidic group and a basic group. Generally, an ion exchanger that is suitable for use with an ion exchange chromatograph and also for deionizing water is suitable for controlled-releasing drugs. Such the ion exchangers are disclosed in "Principles of Ion Exchange" (pp: 312-343) and "Techniques and Applications of Ion-Exchange Chromatography" (pp: 344-361) of Chromatography (E. Heftmann, compilation), van Nostrand Reinhold Company, New York (1975) by H. F. Walton.

Examples of the polar resin of the present invention preferably include agarose, cross-linked dextran (sephadex) or cross-linked agarose (sepharose) having DEAE (Diethylaminoethyl)-group; agarose, sephadex or sepharose having CM (Carboxymethyl)-group; agarose, sephadex or sepharose having trimethylammonium-group; a resin having sulfonyl- or sulfonic acid derivatives as a functional group; a polar resin of hydroxyapatite granules or polystyrene structure. However, the present invention is not limited thereto.

According to an embodiment of the present invention, the resin bonded with proteins through a hydrophobic interaction preferably includes 4 to 10 hydrocarbon chain, but the present invention is not limited thereto.

According to an embodiment of the present invention, multiple resins having different polarities are preferably arranged in the patch. As for the multi-array patch, it is more preferable that a polar resin having a positive charge is first contacted to a diseased area and a polar resin having a negative charge is arranged on the back side. However, the present invention is not limited thereto.

According to an embodiment of the present invention, such a skin disease includes an atopic dermatitis, eczema, psoriasis, a contact dermatitis, erythema, Lichen, chronic or contact urticaria, nodlaris (prurigo nodlaris), and a slight burn or scald that does not damage the stratum corneum. However, the present invention is not limited thereto.

According to an embodiment of the present invention, more preferably, the patch of the present invention further includes disaturated phospholipids, organic acids and divalent cations. The disaturated phospholipids are a disaturated phospholipid derived from an animal lung, and a typical example thereof includes DPPC, DPPI, and the like. A typical example of the organic acids includes an organic acid constituting T.C.A cycle, such as a citric acid, and a typical example of the divalent cations includes calcium and magnesium ions.

In addition, the present invention provides an external patch including a) a polymer matrix having a micro-mesh structure; and b) a polar resin included in the matrix, in which the external patch can absorb blood proteins that are exuded to skin.

In addition, the present invention provides a patch for treating skin diseases or alleviating symptoms of the skin diseases involving an exudation of blood proteins, in which the patch is produced by directly fixing a functional group that is bonded with the proteins to a fabric, a pad, or gauze.

According to an embodiment of the present invention, the functional group that can be directly fixed to a fabric, a pad or gauze may be preferably DEAE-, CM-, trimethylammonium-group or sulfonic acid, or a functional group having C4 to C10, a length of a hydrocarbon chain. However, the present invention is not limited thereto.

In addition, the present invention provides an external patch produced by directly fixing a functional group that is bonded with the proteins to a fabric, a pad or gauze, in which the external patch can absorb blood proteins that are exuded to skin.

In addition, the present invention provides a patch for removing a protein waste product that is secreted to skin, in which the patch includes a) a polymer matrix having a micro-mesh structure; and b) a polar resin bonded with the protein included in the matrix and/or a resin bonded with the protein through a hydrophobic interaction.

In addition, the present invention provides a patch for diagnosing skin diseases involving an exudation of blood proteins, in which the patch includes a) a polymer matrix having a micro-mesh structure; and b) a polar resin bonded with the protein included in the matrix and/or a resin bonded with the protein through a hydrophobic interaction.

As illustrated in Experimental Example 5 and FIG. 6e of the present invention, there is a distinct difference between a protein profile exhibited in a patient suffered from psoriasis and a protein profile exhibited in a patient suffered from an atopic disease. Ig or albumin protein is an example of the protein profiles. A difference between two diseases can be definitely distinguished by using the proteins profiles described above. It is possible to find marker proteins of various skin diseases by using the absorption method or diagnosis various skin diseases by standardizing the protein exudation pattern.

Hereinafter, the present invention will be described.

The present invention relates to a patch for absorbing and then removing blood proteins exuded that permeated into a skin tissue by directly applying it to a diseased surface of skin diseases (for example, an atopic dermatitis, eczema, psoriasis, a contact dermatitis, and the like) involving a symptom of blood protein exudation. The patch removes proteins exuded from the epidermal tissue to reduce an inflammation of the skin, and at the same time, allows water to be maintained in the skin, so that the skin diseases are quickly and safely treated or alleviated. The patch has a matrix that can include water by using a polymer having a micro-mesh structure that can sufficiently pass through extra-vescicular exuded proteins and peptides, for example, a foaming sponge of agar (or agarose), polyacrylamide, latex or polyurethane. The patch is to remove proteins and peptides permeated to the skin by fixing various charged resins (Diethylaminoethyl)-cellulose and CM (Carboxymethyl)-cellulose generally used for a protein chromatograph, a carbohydrate complex (derivatized-complex carbohydrate compounds) with other charged groups, charged resins of hydroxylapatite granules and polystyrene structure, and the like) with a large surface area due to small particles in the matrix structure and then bonding the proteins and peptides permeated to the skin. The present invention is based on the hypothesis that with respect to skin diseases such as an atopic dermatitis and psoriasis, blood proteins are exuded from blood vessel due to a disorder of lipid metabolism and an imbalance of lipid ingestion, and then various inflammatory responses, skin lesion, and hyperplasia of epidermal cell are exhibited due to the exudation described above. The present invention suggests a method for quickly and safely treating an atopic dermatitis, eczema, psoriasis, and diseases having the similar symptoms by suggesting a therapeutic possibility of very severe atopic diseases within 10 days through using a patch that can absorb and then remove blood exuded proteins and peptides permeated in the skin tissue by absorbing the blood exuded proteins and peptides with a fixed resin. Furthermore, the present invention gives a chance to newly understand the diseases described above, and provides various applications using the developed patch.

It is believed that similar diseases such as an atopic dermatitis, eczema, and psoriasis may be caused by a disorder of lipid metabolism and an imbalance of lipid metabolism, and as a result, blood proteins are exuded, and various inflammatory responses or hyperplasia of epidermis cell may be generated due to the blood proteins permeated in the tissue. The present invention provides a method for very quickly and effectively treating skin diseases by removing the exuded proteins through applying a patch to a diseased area by fixing various resins, for example, DEAE-cellulose (or agarose), resins having CM-group, and hydroxylapatite, Dowex resin, and the like in the agar gel, or applying a wet-dressing after bonding a charged group capable of bonding with proteins to a pure cotton fabric.

Effect

As confirmed in the present invention, it is believed that the patch and protein absorption fabric for a wet-dressing according to the present invention are the safest treatment method because any other drugs or specific components are not added to the epidermis, other than distilled water, to treat an atopic disease. It is expected that the treatment method capable of treating severe atopic diseases within 10 days according to the present invention can provide a diversity of new treatment methods and new understanding about causes of atopic diseases.

DESCRIPTION OF DRAWINGS

FIG. 4 is a photograph illustrating an application of the patch to atopic eczema, in which the patch was applied to a top side of the foot of 36 year old male suffered from severe atopic eczema. A 2.5% (w/v) agar gel (thickness of 2 mm) containing 10% (w/v) DEAE-cellulose was applied. The time of applying the patch was from 8 to 9 p.m. to 8 a.m. every day. It was observed that the symptom was remarkably improved at one day after applying the patch and then since three days, the symptom was improved to a certain extent, in which a boundary of the diseased area was hard to ascertain. FIG. 5 is a photograph illustrating an analysis of SDS-PAGE of the proteins absorbed on the patch according to the present invention, in which the patch attached to the patient suffered from atopic eczema was cut in a certain size, dissolved in a SDS-PAGE sample buffer, and then subjected to an electrophoresis apparatus. 10% (w/v) polyacrylamide gel was used, and the proteins were color-developed with CBB-R250. It was found that among the absorbed proteins, the main protein was serum albumin (66 KDa) and immunoglobulin (heavy chain 52 KDa and light chain 27 KDa). The proteins in the $7^{th}$ line were a profile of the total serum proteins. The biggest difference with the exuded proteins obtained from the diseased area is that there were the proteins with 200 KDa or more. While the amount of exuded protein (or the amount that can be the amount of exuded proteins bonded to the patch) permeated into the skin tissue was sharply decreased, the condition of the diseased area was quickly improved. It is confirmed that the phenomenon of protein exudation is closely related to a severity of an atopic disease.

FIG. 6 illustrate an example of applying the patch to a severe atopic dermatitis (a knee area), in which the patch constituted of a 2.5% agar gel (thickness of ~2 mm) containing particles of 10% (w/v) DEAE-cellulose was applied to a 7 years old boy showing a severe atopic dermatitis symptom. The patch was applied to the patient when sleeping at night. The condition of severe skin was remarkably improved from day to day. Pruritus was continued to 4 days after applying the patch, but at 8 days, it was found that there were no symptom of pruritus and epidermis was substantially normalized.

FIG. 7 is a photograph illustrating an analysis of exuded proteins bonded to the patch applied to the knee of the child patient suffered from a severe atopic dermatitis. The patches released from the diseased area were daily cut in a certain size at a regular hour, and then subjected to a SDS-PAGE to visualize the proteins that were diffused from epidermis and then bonded to a polar resin. It was found that a main protein was serum albumin and immunoglobulin. As a result, it was confirmed that the amount of the exuded proteins was closely related to the recovery of diseased area.

FIG. 8 illustrates an example of applying the patch to the child patient suffered from a severe atopic dermatitis (calf area). The result was observed after applying the patch to the calf area of 7 years old boy suffered from an atopic dermatitis. The patch was a 2.5% agar gel containing 10% (w/v) DEAE-cellulose, which was prepared to be 10 mg/ml pig lung extracted phospholipid, 1.5 mM $CaCl_2$, and 5 mM citrate/citric acid (pH 5.8) in water of the gel. Such a component is a "composition suppressing an exudation of blood proteins" used in Patent (Korean Patent No. 0891595, Australia Patent No. 2006217261, PCT No. PCT/KR2006/000638). It was easily confirmed that the patch containing phospholipid as described above exhibits more stable treatment effect (FIG. 6) as compared with the patch that only contains water.

FIG. 9 illustrates an analysis of exuded proteins absorbed to the patch applied to the calf of child patient suffered from a severe atopic dermatitis. As compared with FIG. 3b, it was confirmed that the patch containing phospholipid can constantly absorb the exuded proteins for a long period of time. It was believed that there was high probability that the phospholipids functions as a mild detergent, so that the agglomerated exuded proteins were smoothly diffused. In addition, there was also probability that citric acid disturbs the bonding of agglomerated proteins to promote the removal of exuded proteins. From a result of SDS-PAGE, it was found that even though many lipids were presented on the patch, the lipids did not interrupt absorption of exuded proteins permeated to the skin. Therefore, it was believed that since a wet-wrapping method over a long period of time may affect skin barrier, even though the patch containing the lipid component capable of protecting the skin barrier was applied, the stable treatment effect of the patch could be obtained. Especially, in order for a more stable treatment, it is believed that it is preferable that a method of mixing "a composition suppressing an exudation of blood proteins" containing phospholipids extracted from a pig lung as a main component with a gel of the patch and then using can be used.

In FIG. 10, the effect of patch was observed after applying the patch to a female student having both side of the face with a severe atopic dermatitis. Since application of the patch, it was easily observed that a quicker recovery was exhibited from day to day. At 4 days after applying the patch, the symptom was improved, so that the boundary of diseased area was not distinguished, and at 8 days, the normal skin condition was recovered.

In FIG. 11, the absorbed proteins collected from the gel of the patch applied to the face were subjected to a SDS-PAGE. It was found that a decrease in the level of the absorbed protein amount corresponded to a recovery degree of epidermis.

FIG. 12 illustrates a skin condition after applying the double patch having different polarities.

FIG. 13 illustrates proteins subjected to a SDS-PAGE, in which the proteins were extracted from the gel of the patch after applying the diseased area.

The patches were prepared to have resins with different polarities, and then applied to the psoriasis area of 28 years old female. The patches were applied for 6 hours, and each effect of the patches was observed based on the thinned degree of the epidermis thickness and epidermis color. (FIG. 14) the gel (thickness of ~2 mm) formed by using only 2.5% (w/v) agar, (FIG. 15) the 2.5% (w/v) agar gel (thickness of ~2 mm) containing 10% (w/v) DEAE-cellulose, (FIG. 16) the 2.5% (w/v) agar gel (thickness of ~2 mm) containing 10% (w/v) CM-cellulose, and (FIG. 17) the 2.5% (w/v) agar gel (thickness of ~2 mm) containing 10% (w/v) hydroxylapatite (bipolar resin) were applied to the psoriasis patient, respectively. The patch containing a DEAE-cellulose exhibited the best effect, and the patch containing a CM-cellulose did not exhibit a distinct effect.

FIG. 18 illustrates a protein pattern obtained from the diseased area of the patient suffered from an atopic dermatitis and a protein obtained from the diseased area of the patient suffered from psoriasis. The result provides the base that such two diseases cause an exudation of proteins, equally, but types of exuded proteins were different.

FIG. 20 is a mimetic diagram of the process by using a method prepared in a laboratory. A DEAE-group was coupled while continuously moving fabrics having various thickness and mesh sizes. It is believed that such a method is capable of applying variously according to skin symptoms.

BEST MODE

Hereinafter, the present invention will be described in more detail with reference to non-limited Examples. However, the following Examples are intended only to illustrate the present invention, and the range of the present invention is not understood to be limited to the following Examples.

Example 1: Preparation and Constitution of Patch for Removing Exudation of Blood Proteins Agar (or agarose) is an experimental material that is often used in a molecular biology, is not subjected to a biodegradation by a vivo enzyme, is edible, and can form in a type of very good gel that does not irritate the skin. Such a type of gel has excellent elasticity, can have a great quantity of water, and also has many merits. In addition, particles with large molecular weight can be easily diffused between micro-meshes formed in the gel, and can be easily moved. Generally, when using agar for an electrophoresis, the diffusion of the proteins with 200 kDa or less are too quick in the gel, so that it is difficult to confirm the bands of the proteins. It means that the micro-mesh structure of agar is very large. Since there are a lot of immunoglobulin (IgG, 150 KDa) and serum albumin (66 KDa) with 200 KDa or less as blood proteins exuded to epidermis, there is no problem regarding a freely diffusion of the proteins in the gel.

Polar resins (for example, resins, such as DEAE-cellulose or DEAE-agarose, CM-cellulose (or agarose) and hydroxylapatite) that bond with the proteins in the gel and fix the proteins in the gel can irritate lung and mucous membrane in a state of powder, but in the case of completely hydrating or swelling, there are no irritation. According to the present invention, unnecessary irritation can be minimized by distributing the particles in the gel, such as agar, fixing, and directly contacting to a diseased area.

The resins to be fixed in the gel, such as agar were immersed in distilled water overnight to sufficiently swell. Each of the resins was washed in the order of 0.1 M NaOH-0.1 M HCl-0.1 M NaOH or 0.1 M HCl-0.1 M NaOH-0.1 M HCl in order to remove contaminant attached to the polar group. The resins without the contaminant were repeatedly washed many times with distilled water, and then the washed resins were autoclaved at high temperature and high pressure (15 minutes, 15 lb/cm$^2$).

Figure 1:
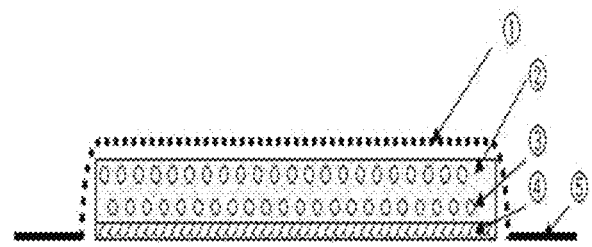
FIG. 1 is a diagram illustrating a constitution of the patch according to the present invention. It is designed that an external patch is closely contacted to a diseased area to absorb blood proteins exuded from blood vessel. 1) A dressing that is an attaching film such as Tegadermm™ manufactured by 3M Co. Ltd. or polyvinylchloride with a porous structure for supplying oxygen to the skin, and has a material capable of properly maintaining water and passing oxygen. 2) A matrix with a micro-mesh structure capable of containing water, such as agar. 3) A resin having a strong polarity, carbohydrate complex (derivatised complex carbohydrate) having a polar group, such as DEAE-cellulose, or a polarity resin such as hydroxylapatite. 4) Cotton gauze or polyester fiber attached on a gel in order to prevent a gel of agar component from being easily broken on a folded part or curved surface of the body. 5) An adhesive tape.
Figure 2:
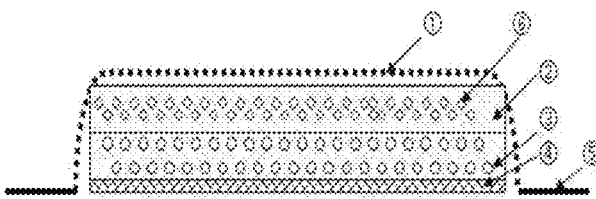
FIG. 2 is a diagram illustrating an example of arrangement of the patch according to the present invention. When resins having different functional groups or having different polarities, for example, DEAE-agarose and CM-agarose are used together, in the case of mixing the resins with the same gel, the resins are bonded with each other, so that there is a high possibility of decreasing protein absorption efficiency. When the polarities are different as described above, it is preferable that two gels be doubly applied to epidermis. Especially, small proteins having a positive charge are effectively absorbed when since most proteins have a negative charge, the polar resin such as DEAE with a positive charge is first contacted to a diseased area, and the resin such as CM is arranged on the back side because of relatively active molecule movement and quick distribution since the proteins having a positive charge have generally small molecular weight (for example, eosinophil cationic protein, 18-22 KDa). 6) A resin having different polarity.
Figure 3:
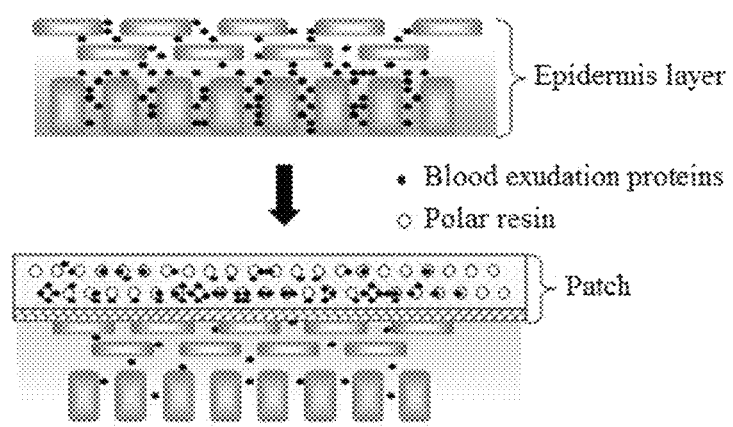
FIG. 3 is a diagram illustrating a functional mechanism of the patch according to the present invention. It is a mimetic diagram illustrating a mechanism that after applying the patch, blood proteins permeated into an epidermal tissue after exuding from blood vessel are diffused to the patch and then bonded to the patch. An inflammation response is alleviated by absorbing the exuded blood proteins to the patch through contacting the protein absorption patch to the epidermis and thus removing the exuded blood proteins, and also the diseased area damaged by an atopic disease or psoriasis can be quickly recovered by maintaining water in the epidermis and also supplementing water.

A process of mixing an agar gel (or agarose gel) with a resin and then fixing was as follows: After the agar gel (2.5% mass/volume ratio) was heated to prepare it in a liquid phase, the temperature was maintained to 60° C. The prepared resin was prepared in a type of filter cake, the water in the resin was removed, and then the mass of the resin was measured to be 10% (mass/volume ratio) of the patch. The agar gel and the resin was homogenously mixed at 60° C., poured to a mold, and then cooled to have a gel thickness of 1.5 mm to 2 mm. Since when the gel, such as agar was applied to the bend part of the body to be excessively folded or bent, the gel may be broken, one-layered cotton gauze (80 to 120 mesh) was applied to the surface of gel to compensate the strength of gel in the state of a liquid gel. A structure and operation principle of the gel is illustrated in the diagram (FIGS. 1 to 3).

Experimental Example 1: Example of Applying to Diseased Area of Atopic Eczema

A patch prepared by fixing 10% (w/v) DEAE-cellulose to 2.5% (w/v) agar gel was applied to a diseased area of the patient (36 years old male) having very severe atopic eczema. The patient was suffered from an atopic eczema for a long period of time, i.e., 10 years or more due to a diseased are of the top of the foot. The patch was not applied during the daytime having many activities, and applied at about 8 to 9 o'clock overnight, and then released at about 8 a.m. The diseased area was observed every day. A gel sample was collected in a certain amount using a cylinder with a diameter of 2 mm from the patch released from the diseased area, and the absorbed proteins were subjected to a 10% (w/v) SDS-PAGE (Sodium dodecyl sulfate-polyacrylamide gel electrophoresis). After performing the electrophoresis, the protein bands were stained with Coomasse brilliant blue-$R_{250}$ staining method.

Figure 4:
FIGS. 4 and 5 are diagrams illustrating an example of application of the patch according to the present invention to atopic eczema.
Figure 5:
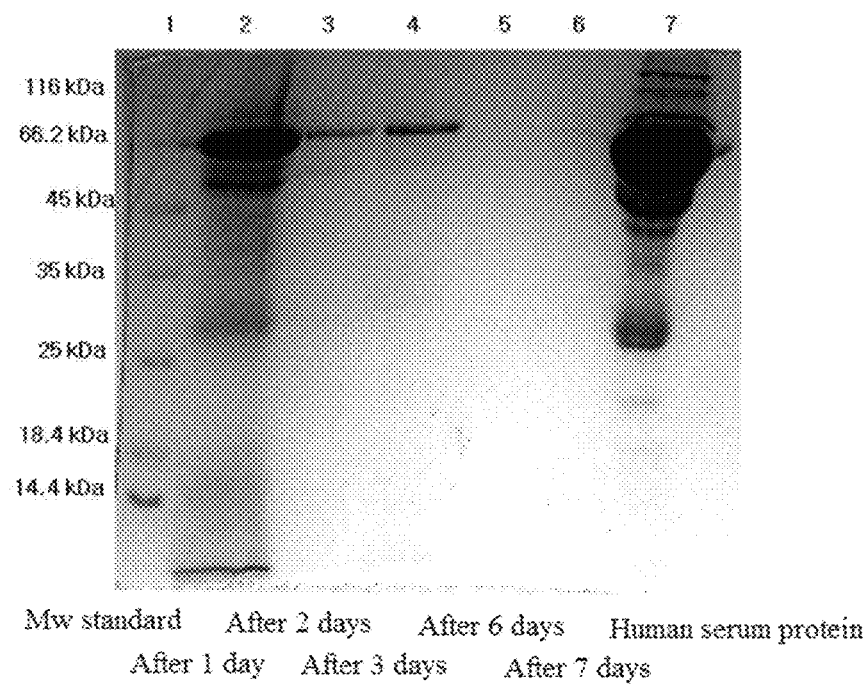
Figure 6:
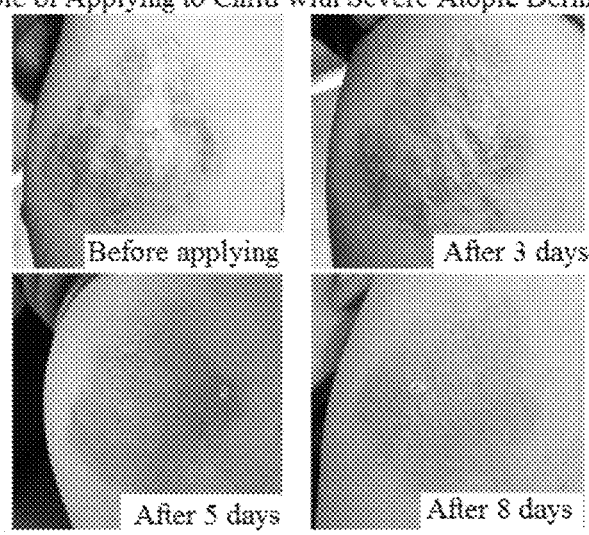
FIGS. 6 to 9 illustrate examples of applying the patch according to the present invention to a typical child patient suffered from a severe atopic dermatitis.
Figure 7:
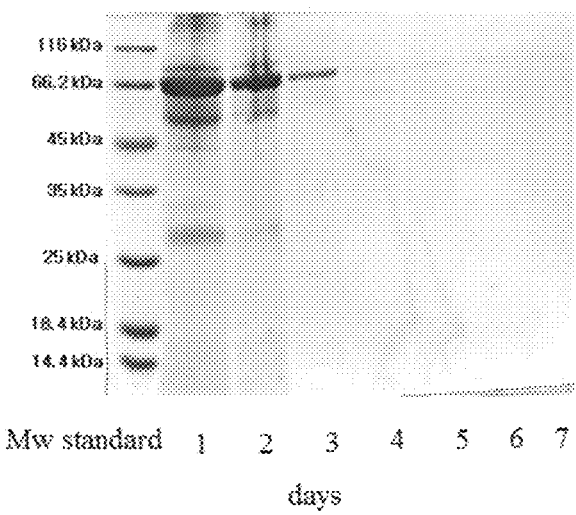
Figure 8:
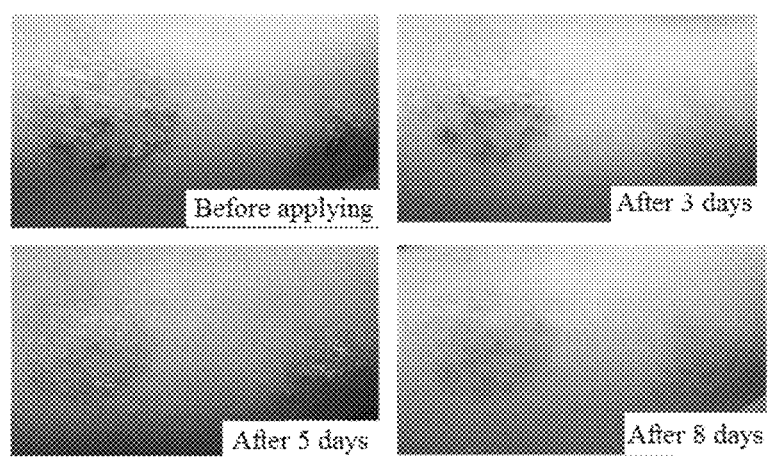
Figure 9:
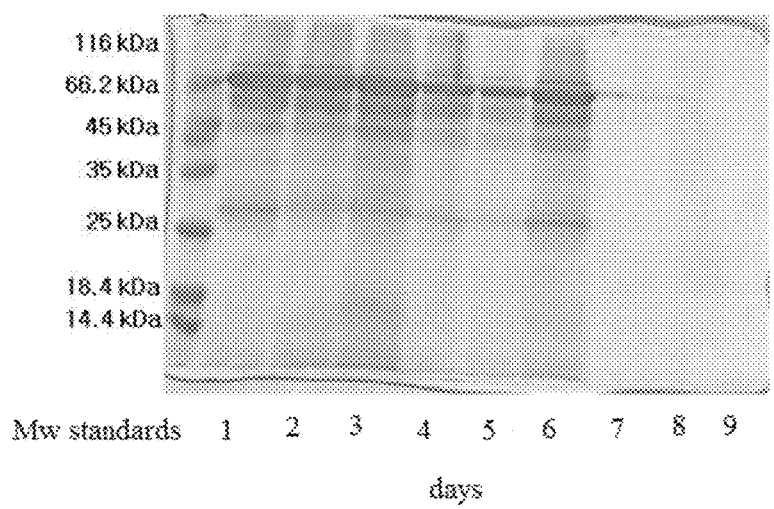
Figure 10:
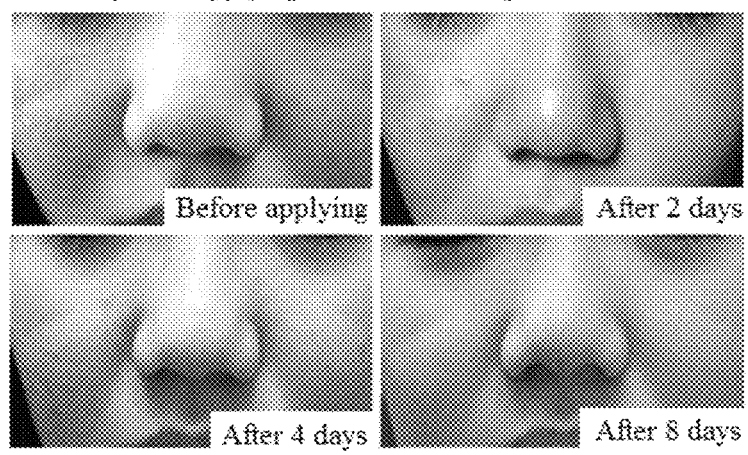
FIGS. 10 and 11 illustrate examples of applying the patch according to the present invention to the face with a severe atopic dermatitis.
Figure 11:
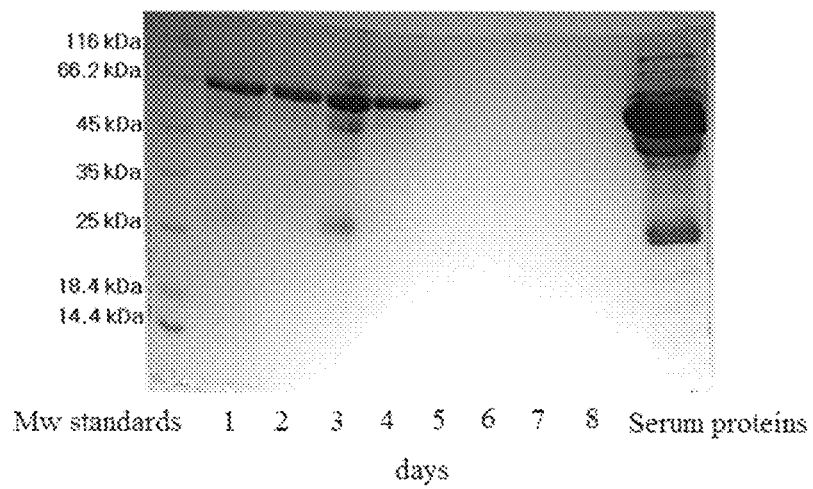
Figure 12:
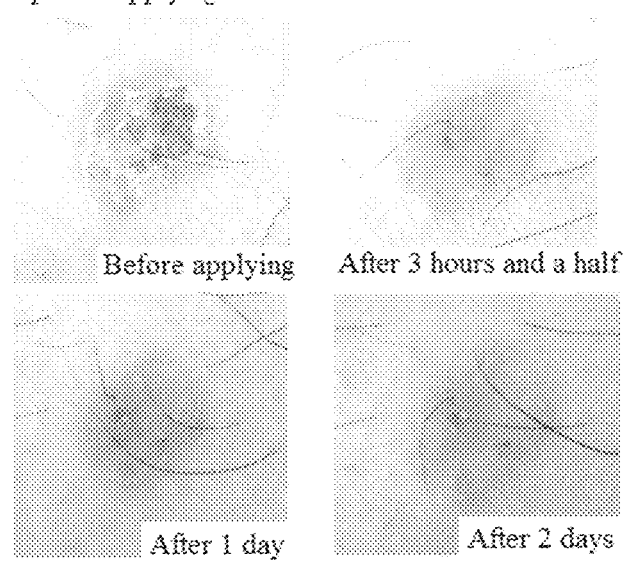
FIGS. 12 and 13 illustrate examples of applying double patch having different polar resins, in which the patch was prepared by arranging 2.5% (w/v) agar gel (~2 mm) containing 10% (w/v) CM-cellulose on 2.5% (w/v) agar gel (thickness of ~2 mm) containing 10% (w/v) DEAE-cellulose (see FIG. 2). The patch was applied to a diseased area of 45 years old male suffered from an atopic eczema, and then the effect and protein absorption degree of the patch were observed by using a SDS-PAGE.
Figure 13:
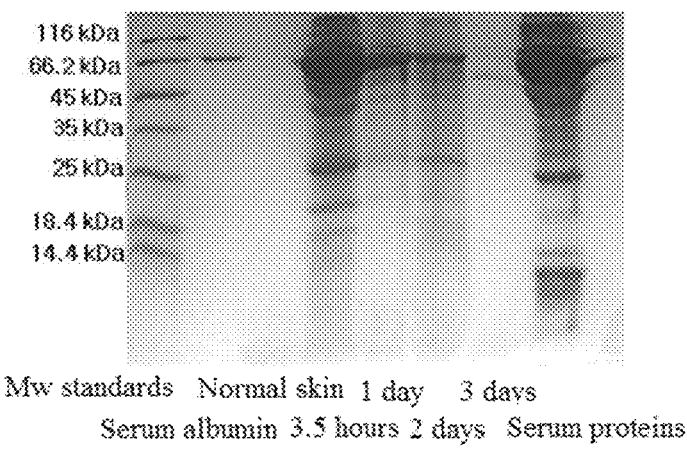
Figure 14:
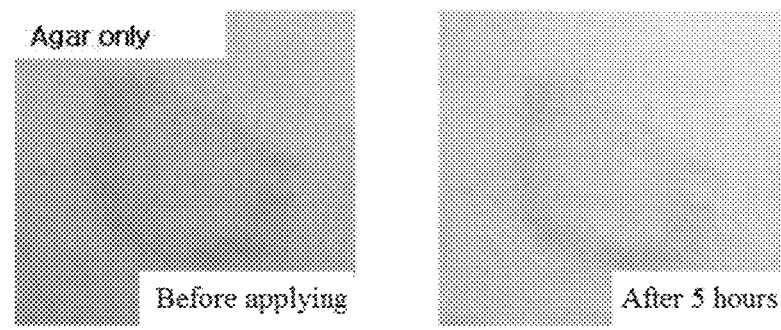
FIGS. 14 to 18 illustrate examples of applying the patch containing various resins to each of diseased areas of the psoriasis patient.
Figure 15:
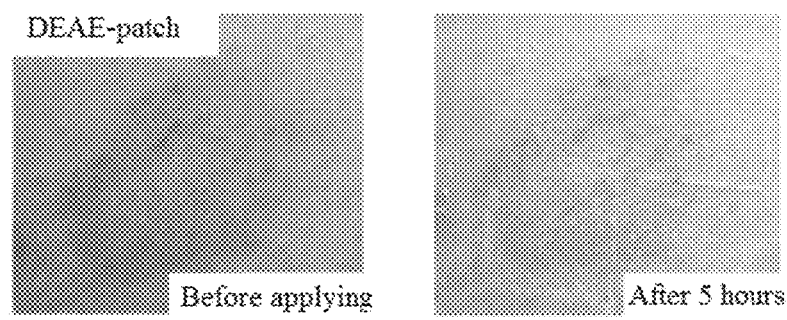
Figure 16:
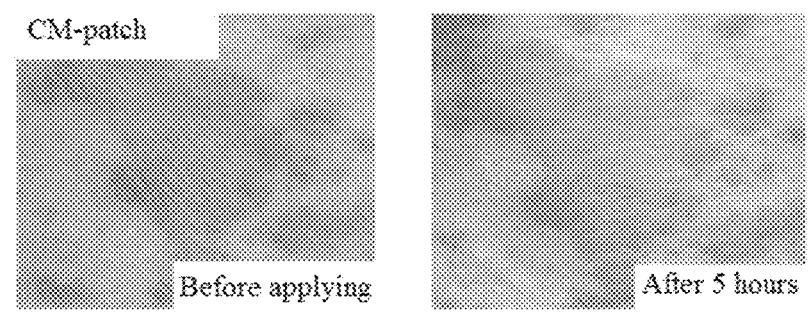
Figure 17:
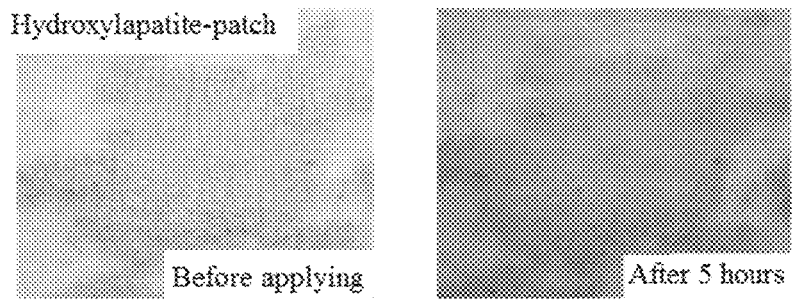
Figure 18:
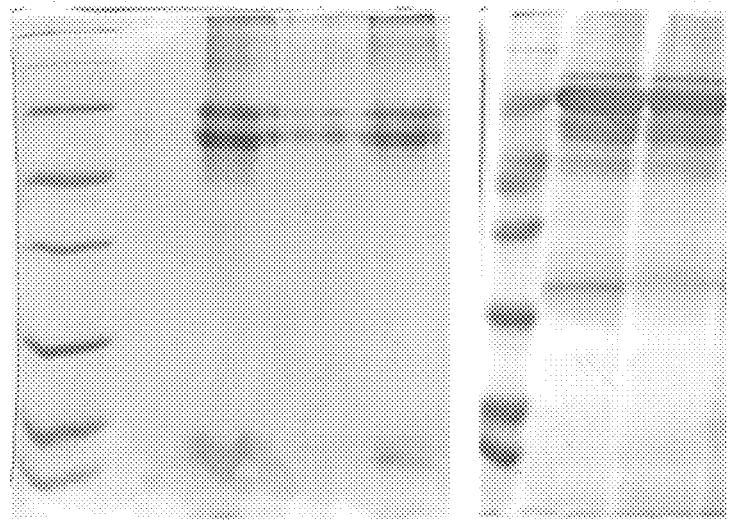

As a result of analyzing the proteins bonded to the patch released from the diseased area, it was found that the largest number of the proteins was serum albumin and the second largest number of the proteins was immune antibody protein (heavy chain ~52 KDa, light chain 27 KDa). The result corresponded to the fact that the exudation of the blood proteins was carried out according to the molecular weight. It was found that when the amount of the protein absorbed to the patch (i.e., the amount of exuded blood protein) was decreased, the condition of the diseased area was dramatically improved. Such a result is an indirect result of verifying that the tissue exudation of the blood proteins promotes an atopic dermatitis. It shows the surprising fact that an atopic skin disease can be treated without any kinds of drugs or treatment drugs showing effectiveness, such as any kinds of steroids, steroid derivatives, drugs of immune control mechanism (for example, Elidel or Tacrolimus), and moistener ointment. The method of the present invention is a very stable method since the treatment time is very short and there are no components to be absorbed to the skin, other than distilled water (FIGS. 4 and 5).

Experimental Example 2: Example of Applying to Severe Atopic Dermatitis of Typical Child (Example Carried Out by Containing Specific Phospholipids in the Patch)

A patch was applied to a partial diseased area of 7 years old boy having severe atopic dermatitis symmetrically on the whole body. Two kinds of the patches were applied. 2.5% (w/v) agar gel (thickness of ~2 mm) containing 10% (w/v) DEAE-cellulose and 2.5% (w/v) agar gel (thickness of ~2 mm) containing 10% (w/v) DEAE-cellulose, 10% (w/v) phospholipids extracted from pig lung, 1.5 mM $CaCl_2$, and 5 mM citrate/citric acid (pH 5.8) were applied to different diseased areas, respectively, and then the effects were compared. The phospholipids extracted from pig lung, 1.5 mM $CaCl_2$, and 5 mM citrate/citric acid (pH 5.8) component is a composition for suppressing an exudation of blood proteins for treating an atopic dermatitis [Korean Patent No. 0891595, Australia Patent No. 2006217261, PCT Patent No. PCT/KR2006/000638], and now Phase III clinical trials have been completed for premising as a new drug. The speed of treatment was observed by applying two kinds of the patches to the diseased area, and the profile of proteins exuded was observed. In addition, it was investigated that the added phospholipids interrupted the diffusion of the protein to the patch.

As a result of applying two kinds of the patches, it was found that all the two kinds of the patches exhibited very significant treatment speed and effectiveness on the child having a typical severe atopic dermatitis. It was found that the patch containing phospholipids, calcium ion, citrate/citric acid salt absorbed the exuded proteins more effectively. It was observed that for the treatment effect, the patch containing the phospholipids extracted pig lung more stably treated the skin and then normalized the skin. It was believed that the phospholipids extracted from pig lung functions as a mild detergent to dissociate the agglomerated proteins exuded and then stimulated to the skin, so that it exhibits more excellent effect of removing an exudation. In addition, there is a possibility that citric acid contained in the composition interrupts the ion bonding that may be between the proteins, so that the exudation can be more effectively removed. It is believed that since the saturated phospholipids contained in the patch has an effect of suppressing an exudation of blood proteins, the phospholipids allow the recovery of the diseased area to be more quickly. By comparing effects of two kinds of the patches (the patch only containing DEAE-cellulose and the patch containing DEAE-cellulose, and phospholipids extracted from pig lung+1.5 mM $CaCl_2$+5 mM citrate/citric acid (pH 5.8)), it was confirmed as an important fact that as a conclusion, the phospholipids do not interrupt exuded proteins to bond to the polar resin particles fixed in the patch.

In order to obtain more quick and stable treatment effect, it is believed that drugs or components having a function of suppressing an exudation of blood proteins are preferably used together.

A wet-wrapping method was used for treating an atopic dermatitis. In order to continuously apply the patch having a great quantity of water according to the present invention, it is believed that a method of applying the patch containing various lipids and components capable of compensating skin barrier may be a good method of relieving the pain of patient suffered from an atopic disease. In addition, it is believed that since it is known that ointments such as steroid or Tacrolimus have an effect of suppressing an exudation of blood proteins in addition to original anti-stress activity and immune decrease function, the increase of treatment effect can be expected when using the patch prepared by mixing a proper amount of drug capable of suppressing an exudation of blood proteins in the matrix of the patch, or when applying the patch while suppressing an exudation of blood proteins by applying the drugs capable of suppressing an exudation of blood proteins before and after applying the patch.

Experimental Example 3 : Example of Applying to Teenager Having Face Suffered from Severe Atopic Dermatitis The result was observed after applying the patch on both of the cheeks of the teenager (16 years old girl) suffered from a severe atopic dermatitis. The patient was suffered from a severe atopic dermatitis, so that the normal life could not be maintained due to a severe itching and burning sensation. An effect of the patch should be tested on the face since neutral fats are secreted in a great quantity through sebum, thereby inhibiting an effect of the patch on absorption of protein. As the patch, 2.5% (w/v) agar gel (thickness of ~2 mm) containing 10% (w/v) DEAE-cellulose was applied. The patch was applied during the sleeping time after dinner, and then released before going to the school a.m. After applying the patch, the symptom were getting better every day, and at 8 days after applying the patch, the skin of face was recovered in a normal state. It was observed that the skin condition of the patient was maintained for about 20 days, and subsequently, both the cheeks were again turned red, and a slight symptom of the atopic disease was caused.

From a result of SDS-PAGE, it was confirmed that a removal of exuded proteins using the patch required about 5 days averagely, and the treatment period required for 8 to 10 days in the case of the severe patient. Especially, it is thought that the amount of antibody protein was decreased and then the symptom was getting better. In conclusion, it is believed that the exuded amount of the blood proteins is directly involved in a serious and slight symptom, and also an atopic disease can be easily treated as long as various and active treatment capable of suppressing an exudation of blood proteins is carried out at the same time.

Experimental Example 4 : Example of Applying Double Gel-Type Patch Containing Resins with Different Polarities A double patch was prepared to have different polarities by applying 2.5% (w/v) agar gel (~2 mm) containing 10% (w/v) CM-cellulose on 2.5% (w/v) agar gel (thickness of ~2 mm) containing 10% (w/v) DEAE-cellulose (see FIG. 2). The patch was applied to a diseased area of 45 years old male suffered from an atopic eczema, and then an effect and protein absorption of the patch were observed. At first day, the patch was applied to the diseased area for 3 hours and a half, and then applied during the sleeping time every day. At 3 hours and a half after applying the patch, the condition was significantly recovered and getting better every day sharply.

It was believed that an amount and the type of the exuded proteins absorbed to the gel were more varied, and also clear, as compared with the case of using only DEAE-cellulose. It was also observed that an effect of treating was much faster.

Experimental Example 5 : Example of Applying to Psoriasis Patient

The effectiveness of patch was observed after applying the patches with various combinations to the skin of 28 years old female having psoriasis caused on the whole body (Especially, the symptom on the limbs, legs and arms regions was worse).

The following gels were applied to the patients with psoriasis, respectively for about 5 hours, and then released. Since then, the diseased areas were observed. The best effect exhibited on the psoriasis patient was 2.5% agar gel patch containing 10% (w/v) DEAE-cellulose and the patch having the worst effect was 2.5% (w/v) agar gel patch containing 10% (w/v) CM-cellulose (see FIGS. 14 to 17).
  a. Gel formed by only 2.5% (w/v) (thickness of ~2 mm)
  b. 2.5% Agar gel containing 10% (w/v) DEAE-cellulose
  c. 2.5% (w/v) Agar gel containing 10% (w/v) CM-cellulose
  d. 2.5% (w/v) Agar gel containing 10% (w/v) hydroxylapatite (bipolar resin).

The most interesting finding was that types of proteins exuded from the diseased areas of the psoriasis patient and atopic disease patient were different. In the case of the patient suffered from psoriasis, albumin was observed, but immunoglobulin was observed in a very small amount. It is believed that when the proteins are exuded from blood vessel, a selective exudation is carried out according to molecular weight. It can be expected that antibody proteins with larger molecular weight than that of albumin are easily not exuded. As a result, it is believed that a reason why the inflammation response is more active in the case of an atopic dermatitis can be described, and a reason why a pathologic mitosis of epidermis cell is caused rather than an inflammation response of psoriasis disease or skin lesion. According to the observations described above, it is possible to easily diagnosis psoriasis and atopic diseases using the patch of the present invention with eyes. That is, when the distinction between the atopic dermatitis and psoriasis are in confusion, the patch of the present invention can be used as diagnostic criteria. Furthermore, by using an immunological research method, researches on various proteins can be possible. From now on, the patch according to the present invention may be used for various applications, such as a research object, in addition to a treatment object.

Experimental Example 6: Example of Applying Patch on External Injury or Wound (Example of Negative Effect of Patch)

Figure 19:
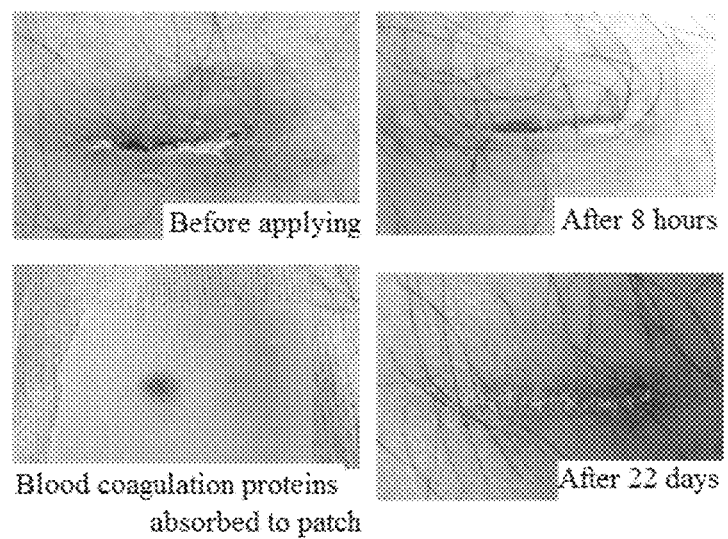
FIG. 19 illustrates a result of an observation after applying the patch constituted of 2.5% agar gel (thickness of ~2 mm) containing 10% (w/v) DEAE-cellulose to the injury caused by a external physical impact, as an example of applying the injury (negative effect). It was believed that even the proteins required for treating the injury were absorbed to the patch, and the patch reduces the speed of treatment of the injury. An absorbed blood and yellow proteins were observed on the patch released after applying for 6 hours. It was observed that after removing the patch, if the epidermis receives a few tensions, bleeding was weakly caused on the diseased area. In addition, it was observed that even if the injury had closed up, a large scar of the injury marked. The patch according to the present invention is not limited to skin diseases exhibiting an exudation of blood proteins, such as an atopic dermatitis or psoriasis without external injury.

The patch was applied to a cut or wound, and then effect thereof was observed. As a result, it was believed that an application of the protein absorption patch to a wound was not preferable. This is because even proteins required for blood coagulation and tissue recovery are absorbed, and after applying for 8 hours, a slight breeding is again caused. Furthermore, the speed of healing the wound was considerably slow, and also it was weak to an inflection since the wound was open. IN addition, even though the wound is close later, the scar may be marked (FIG. 19).

Experimental Example 7 : Application of Patch Using Patch Property (Method of Using by Bonding Polar Group to Carbohydrate of Cotton Fabric)

In the case of preparing and using a resin as a type of patch, it is difficult to reuse the resin such as agarose with a polar group such as DEAE-cellulose. Since a complex carbohydrate resin with a substituent (Derivatised complex carbohydrate) has a wide surface area and a high protein bonding ability, the effect can be obtained when the resin is used by fixing it in a patch in a type of gel. However, it has a disadvantage that it is a little expensive. In order to compensate such a problem, it is possible to use it by bonding various polar groups and DEAE-group to 100% cotton fabric. Since a chemically modified fabric capable of bonding protein has a good elasticity, the fabric can be used by contacting to the bend part of body, and if the absorbed proteins are effectively removed, it can be re-used repeatedly. The protein bonding ability of the fabric is a little reduced as compared with the resin for purifying proteins, but the fabric can be variously applied. Especially, the tailored treatment can be possible by further adding various drugs (for example, disinfectant, antibiotic, an antihistaminic agent, steroid, and the like) and various lipids (for example, ceramide, phospholipids, lipid mixture in a type of liposome, and the like) on a doctor's advice. When it is prepared as a type of cloth, it can be expected that the fabric can be easily used for treating a patient suffered from a whole body atopic disease.

The present invention provides a method for easily preparing a fabric capable of absorbing proteins through bonding DEAE-group to a cotton fabric.

The process of preparing DEAE-cotton fabric according to the present invention is as follows:
  1) Drying a cotton fabric after washing it with distilled water;
  2) Immersing the cotton fabric thus dried in 3M NaOH for 30 seconds;
  3) Immersing the cotton fabric thus obtained in a mixed solution of 3M NaOH and 3M DEAE-Cl (diethylaminoethyl chloride) for 40 minutes;
  4) Immersing the cotton fabric thus obtained in 3M DEAE-Cl;

5) Washing the cotton fabric thus obtained with distilled water; and
6) Drying the cotton fabric thus obtained.

Figure 20:
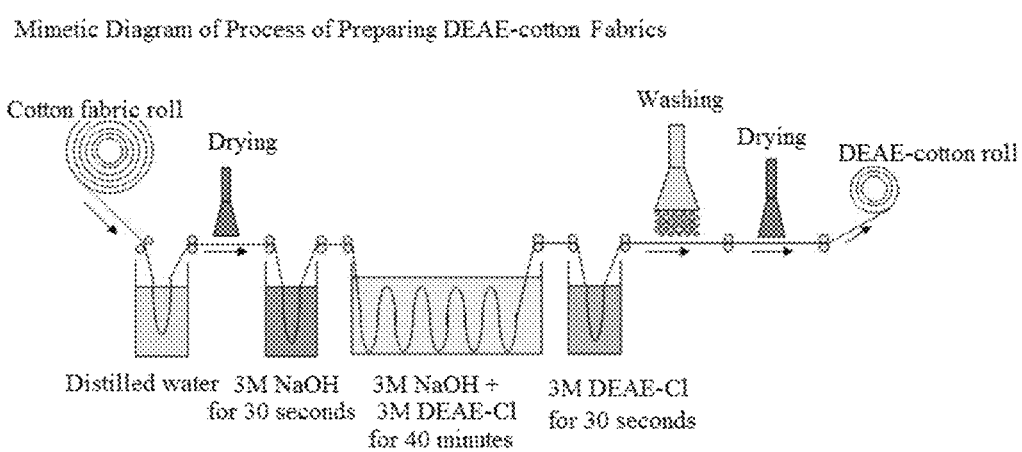
FIG. 20 is a mimetic diagram illustrating a process of producing DEAE-cotton fabrics. A method of bonding a DEAE-group to cellulose was optimized in order to use a cotton fabric coupling a DEAE-group for treating an atopic skin disease or psoriasis disease, and also the production method was simplified for a bulk production.

When the DEAE-cotton fabric is prepared in a bulk production as described above, the method can be possible by using the mimetic method as disclosed in FIG. 20. The more effective patch can be prepared in a cheap cost, and thus it can be helpful for many patients, so that the present inventors simplified the process of preparing.

The DEAE-cotton fabric prepared by using the process as disclosed above was contacted to a diseased area of a patient with an atopic disease for about 4 hours, and then absorption of exuded proteins was confirmed.

Figure 21:
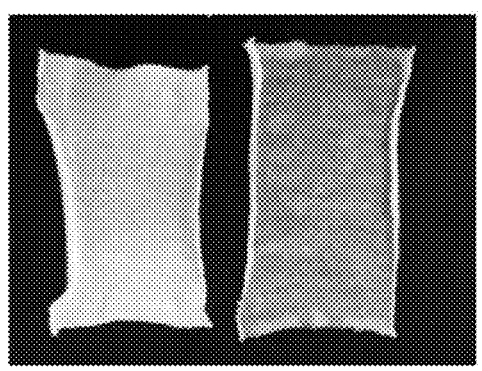
FIGS. 21 and 22 are photographs illustrating an exuded protein absorption using a DEAE-cotton fabric. A DEDE-cotton fabric was prepared by coupling a DEAE-group to a general cotton fabric. A left side in FIG. 12 was a type of drying, and a right side was a type of wetting with distilled water before applying a diseased area. A exuded protein absorption was confirmed by applying the fabric to the diseased area of atopic eczema. It was easily confirmed that a small amount of proteins was detected on the general cotton fabric, but a great quantity of various blood exuded proteins were detected (FIG. 22). Such the fabric capable of bonding the protein or polar group can be applied to the diseased area with a sharp bend. In addition, it can be expected that in the case of having the whole body having dermatitis, it can be prepared in a type of cloth, so that the whole body can be more effectively treated. Furthermore, it is expected that since in the case of the fabric, since various drugs can be mixed and then used, tailored treatment can be carried out by medical specialists in a way of adding liquid drugs according to the conditions of patient.

FIG. 21 illustrates a DEAE-cotton fabric, in which the left side is the fabric in a state of drying and the right side is the fabric in a state of wetting using distilled water before applying it to a diseased area.

Figure 22:
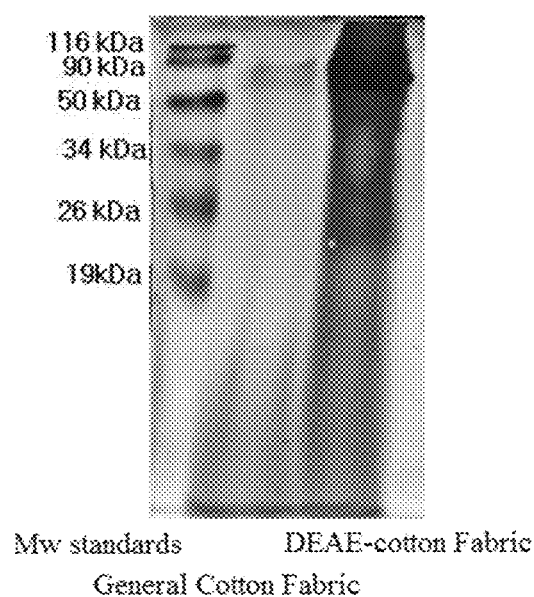

As illustrated in FIG. 22, a general cotton fabric and DEAE-cotton fabric were contacted to a diseased area for 5 hours, respectively. After releasing the fabrics, the same size of the fabrics was cut, and then the absorbed proteins were confirmed by using a SDS-PAGE. It can be confirmed that the cotton fabric with DEAE-group can absorb and then remove an exudation of blood proteins from the diseased area, in which the effect is not significantly different from that of the agar gel patch containing DEAE-cellulose.

A cotton fabric having DEAE-group or other polar groups can be used for treating an atopic disease, psoriasis, and other similar diseases. In addition, it is expected that the above cotton fabric can be used for structurally removing waste products from the skin. In some cases, it can remove specific lipids or poorly water-soluble proteins by bonding with an octyl group, a butyl group, and the like. Accordingly, in addition to an object of treatment, it can be used for an object of beauty treatment (for example, materials for beauty masks), and especially, it is economical and also eco-friendly since it can be used repeatedly.

The invention claimed is:

1. A method of treating skin diseases involving an exudation of blood proteins, the method comprising:
   applying a patch to a skin-diseased area of a subject in need thereof, wherein the patch comprises:
   a) a polymer matrix with a mesh structure capable of absorbing the blood proteins; and
   b) a plurality of polar resins including a first polar resin and a second polar resin capable of binding with the blood proteins contained in the matrix through hydrophobic interaction,
   wherein the first polar resin has a polarity different from the second polar resin, and wherein the first resin located on a skin-contacting side of the patch has a positive charge, and the second resin located on the opposite side of the patch has a negative charge.

2. The method of treating the skin diseases according to claim 1, wherein the polymer matrix with the mesh structure is a micro-mesh structure of a complex carbohydrate selected from the group consisting of agar and agarose, or a micro-mesh structure produced by using polyacrylamide, latex, polystyrene, polyvinyl chloride, silicone polyurethane, or cellulose fiber.

3. The method of treating the skin diseases according to claim 1, wherein at least one of the plurality of polar resins is agarose, cross-linked dextran, or cross-linked agarose having DEAE (Diethylaminoethyl)-group; agarose, cross-linked dextran, or cross-linked agarose having CM (Carboxymethyl)-group; agarose, cross-linked dextran, or cross-linked agarose having trimethylammonium-group; a resin having a functional group selected from sulfonyl- or sulfonic acid derivatives; or a polar resin (charged resin) of hydroxylapatite granules or polystyrene structure.

4. The method of treating the skin diseases according to claim 1, wherein the at least one of the plurality of polar resins contains a C4 to C10 hydrocarbon chain.

5. The method of treating the skin diseases according to claim 1, wherein the skin disease includes an atopic dermatitis, eczema, psoriasis, a contact dermatitis, erythema, Lichen, chronic or contact urticaria, nodlaris (prurigo nodlaris), and a slight burn or scald that does not damage the stratum corneum.

6. The method of treating the skin diseases according to claim 1, wherein the patch further includes disaturated phospholipids, organic acids, and divalent cations.

7. The method of treating the skin diseases according to claim 1, wherein the patch further includes triacylglycerol, seramide, seramide derivatives, complex lipids extracted from animals, or synthetic lipids.

* * * * *